United States Patent [19]

Bornengo et al.

[11] Patent Number: 4,772,756
[45] Date of Patent: Sep. 20, 1988

[54] PROCESS FOR THE PREPARATION OF FLUOROALKYL PERFLUOROVINYL ETHERS

[75] Inventors: Giorgio Bornengo; Michele Pontevivo, both of Novara; Antonio Marraccini, Dormelletto; Silvana Modena, Monza, all of Italy

[73] Assignee: Ausimont S.p.A., Milan, Italy

[21] Appl. No.: 95,674

[22] Filed: Sep. 14, 1987

[30] Foreign Application Priority Data

Sep. 19, 1986 [IT] Italy .............................. 21759 A/86

[51] Int. Cl.⁴ ............................................. C07G 41/18
[52] U.S. Cl. ...................................... 568/684; 568/615; 568/685
[58] Field of Search .................... 568/615, 684, 685

[56] References Cited

U.S. PATENT DOCUMENTS 3,291,843 12/1966 Fritz et al. ........................... 568/685
3,321,532 5/1967 Lorenz ................................. 568/685
4,515,989 5/1985 Ezzell et al. ........................ 568/685

Primary Examiner—Howard T. Mars
Attorney, Agent, or Firm—Stevens, Davis, Miller & Mosher

[57] ABSTRACT

A process for the preparation of fluoroalkyl ethers of the formula:

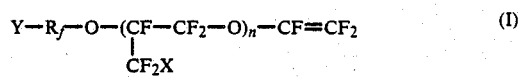

wherein:
Y is Br or F;
X is F, Cl or Br or their mixtures when n is equal to or higher than 2;
n is within the range of from 0 to 4;
$R_f$ represents a perfluoroalkylene radical containing from 1 to 8 carbon atoms.

The process is characterized in that a fluoroalkoxy perfluoroacyl fluoride of the formula:

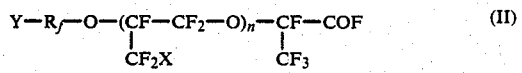

is slowly heated with a salifying agent and a solvent, in the presence of a catalytic amount of N,N-dimethylformamide, with an end temperature within the range of from 60° to 150° C. being reached.

9 Claims, No Drawings

PROCESS FOR THE PREPARATION OF FLUOROALKYL PERFLUOROVINYL ETHERS

DESCRIPTION OF THE INVENTION

The present invention relates to the preparation of fluoroalkyl perfluorovinyl ethers. More precisely, it relates to a process for the preparation of fluoroalkyl perfluorovinyl ethers having the formula:

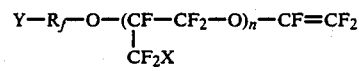

wherein:
Y is Br of F;
X is F, Cl or Br or their mixtures when n is equal to or higher than 2;
n is within the range of from 0 to 4;
$R_f$ represents a perfluoroalkylene radical containing from 1 to 8 C atoms.

The fluoroalkyl perfluorovinyl ethers are useful as monomers for copolymerization with fluorinated olefins, and in particular tetrafluoroethylene, vinylidene fluoride and hexafluoropropene.

The introduction of these vinyl ethers in the so-obtained plastic polymers leads to better properties of processability of the polymers, and a higher flexibility of the manufactured articles.

Furthermore, when Y is Br, a potentially reactive site is inserted into the polymer which may be used for additional reactions which otherwise would not be possible in perfluorinated materials. The thus-obtained polymers may be used, e.g., in chlorine-alkali cells, as ion-exchange membranes.

The preparation of the fluoroalkyl perfluorovinyl ethers is known starting from the corresponding acyl fluorides by decarboxylation of the acyl fluoride by heating up to 300° C. in the presence of activators, such as ZnO and SiO₂, and possibly in the presence of salifying agents. But such a synthesis route involves the formation of considerable amounts of secondary and tertiary isomers of the vinyl ether, as described in U.S. Pat. No. 3,896,179, i.e., compounds of the types:

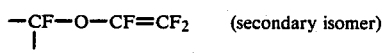

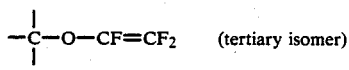

The presence of these isomers in the vinyl ether is highly undesirable, because they can act as chain-transfer agents in the subsequent copolymerization, giving rise to copolymers with a too low molecular weight.

Also processes are known which involve a salification of the acyl fluoride with salifying agents of the sodium carbonate type, in solvents of the glyme type, and a subsequent decarboxylation, e.g., at 100°–150° C. These processes can be schematically shown as follows:

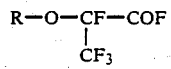

wherein R is a fluoroalkyl radical

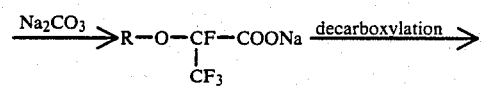

One of these processes is disclosed in U.S. Pat. No. 3,291,843.

When the vinyl ether is obtained by means of one of these processes, it may contain considerable amounts of hydrogenated byproduct, of the

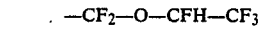

type.

The presence of hydrogenated products at a concentration higher than certain levels involves the presence of particularly reactive sites

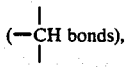

which are undesirable in the copolymerization process. It has furthermore been verified that copolymers obtained from vinyl ethers polluted by hydrogenated byproducts show insurmountable problems in the extrusion process, and lead to the obtention of manufactured articles having clearly unsatisfactory applicative properties.

An object of the present invention is therefore to provide a process for the preparation of fluoroalkyl perfluorovinyl ethers of formula (I) by starting from the corresponding acyl fluorides, wherein the obtained product is free from secondary and tertiary isomers, and is substantially free from hydrogenated byproduct.

Another object is to provide a process which gives very high yields of fluoroalkyl perfluorovinyl ethers.

These and still further objects are achieved by the process of the present invention for the preparation of fluoroalkyl perfluorovinyl ethers of formula (I).

The process is characterized in that a fluoroalkoxy perfluoroacyl fluoride of formula:

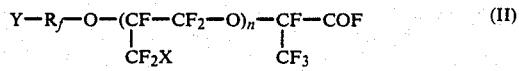

is slowly heated with a salifying agent and a solvent, in the presence of a catalytic amount of N,N-dimethylformamide, reaching an end temperature within the range of from 60° to 150° C.

In accordance with the present invention, it has been discovered that by operating in the presence of catalytic amounts of N,N-dimethylformamide and slowly heating up to a temperature within the range of from 60° to 150° C., the thus-obtained product is free from secondary and tertiary isomers, and is substantially free from hydrogenated byproduct; and furthermore very high yields are obtained.

By the expression "substantially free" from hydrogenated byproduct, it is meant that such byproduct is present in a maximum amount not higher than 5% by weight in the reaction products. Often, it is present in an amount not higher than about 0.5% by weight.

The amount of N,N-dimethylformamide is generally within the range of from 0.1 to 20% by weight relative to the acyl fluoride (II), and preferably in the range of from 0.5 to 5%.

Especially suitable organic solvents are those of the glyme type.

Especially suitable salifying agents for the acyl fluoride (II) are the alkali metal carbonates and alkaline-earth metal carbonates.

The amount of salifying agent is not critical. It may range from the stoichiometric amount to an excess, e.g., about 50%, relative to the stoichiometric amount.

For the purpose of obtaining a vinyl ether having a high purity level, it is necessary to thoroughly dry the solvent and the salifying agent.

Starting from an acyl fluoride (II) wherein the value of n is zero is preferred. Also starting from an acyl fluoride wherein the radical $R_f$ contains from 2 to 3 C atoms is preferred.

The heating of the reaction mixture takes place slowly, until the end temperature within the range of from 60° to 150° C., and preferably in the range of from 110° to 140° C., is reached. Usually, the heating of the reaction medium, to maintain it at the end temperature, is continued over a certain time, e.g. over 2 to 8 hours.

The duration of the slow heating step is, e.g., from 1 to 6 hours.

The following examples are supplied for the purpose of illustrating the invention without thereby limiting it.

EXAMPLE 1

In the present example, to be compared to Example 2, N,N-dimethylformamide is not used.

To a 250-ml reactor equipped with stirrer, thermometer, and distillation column with condensor, 50 ml of anhydrous diglyme and 50 g of anhydrous $K_2CO_3$ are charged.

At room temperature, 83 g (0.25 mol) of 2-perfluoropropoxy-perfluoropropionyl fluoride

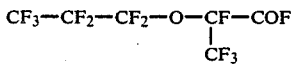

are slowly added in such a way that the temperature of the reaction mixture does not exceed 30° C.

The reaction mass is then heated 1 hour at 35° C., then 1 hour at 45° C., and 1 hour at 60° C.; now it is possible to start the product refluxing through the distillation column.

For completing the reaction, the mixture is kept heated at 120° C. for 6 hours.

Fifty-eight grams of a reaction product was obtained, which was identified by $^1$H-N.M.R. and $^{19}$F-N.M.R. analyses, and mass-spectrophotometry.

80% of product is constituted by perfluoropropyl vinyl ether (46.4 g=0.174 mol) and the residual 20% thereof is heptafluoropropyl 1,2,2,2-tetrafluoroethyl ether ($C_3F_7$—O—CFH—$CF_3$) (11.6 g). Reaction conversion=100%, selectivity to and yield of perfluoropropyl vinyl ether=69.7%.

During the reaction, small amounts of unidentified uncondensable products are formed.

EXAMPLE 2

To a reaction equipment analogous to that described in the preceding Example 1, 50 ml of anhydrous diglyme, 1 ml (0.994 g) of N,N-dimethylformamide, and 50 g of anhydrous $K_2CO_3$ are charged.

At room temperature, 83 g (0.25 mol) of 2-perfluoropropoxy perfluoropropionyl fluoride are slowly added in such a way that the temperature of the reaction mixture does not exceed 30° C.

The reaction mass is then heated 1 hour at 35° C., then 1 hour at 45° C., and 1 hour at 60° C.; now, it is possible to start to draw the product refluxing through the distillation column.

For completing the reaction, the mixture is kept heated at 120° C. for 6 hours.

64.4 grams were obtained of a reaction mixture, which is constituted by:

64.07 g of perfluoropropyl vinyl ether;
0.32 g of heptafluoropropyl 1,2,2,2-tetrafluoroethyl ether.

Conversion: 100%, selectivity to and yield of perfluoropropyl vinyl ether: 96%.

EXAMPLE 3

In the present example, to be compared to Example 4, no N,N-dimethylformamide is used.

Five hundred ml of anhydrous diglyme and 400 g of anhydrous $Na_2CO_3$ are charged to a 2,000-ml four-neck flask equipped with stirrer, thermometer, dropping funnel and reflux condenser connected to a Claisen distillation apparatus.

860 g are added dropwise of acyl fluoride

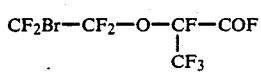

with the inner temperature being maintained at approximately 20° C. During the addition time, gas evolves. After the end of the dripping, stirring is continued for 1 hour. The heating is then started, with the temperature being progressively increased up to 130° C.: 1 hour at 80° C., 1 hour at 100° C., 1 hour at 120° C. The evolution of gas starts again at 130° C. Now it is possible to start to draw off the product, which is collected inside a trap cooled at −78° C.

For completing the reaction, the reaction mixture is kept heated at 130° C. for 3 hours.

The collected product is purified by fractional distillation. 400 grams are obtained of a fraction boiling at 56°–57° C., which contains 89.3% by weight of

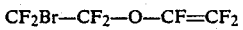

and 10.7% by weight of

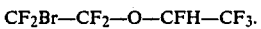

The products were characterized by I.R. spectroscopy and $^{19}$F-N.M.R. and $^1$H-N.M.R.

EXAMPLE 4

The preparation is carried out according to the procedures of Example 3, by using 500 g of anhydrous $Na_2CO_3$, 600 ml of anhydrous diglyme, 1,000 g of the same acyl fluoride of Example 3, and 10 g of N,N-dimethylformamide. 650 g are obtained of a product which is constituted by 96% by weight of $$CF_2Br-CF_2-O-CF=CF_2$$

and 4% by weight of hydrogenated byproduct.

The products were characterized by I.R. spectroscopy and $^{19}F$-N.M.R. and $^1H$-N.M.R.

What is claimed is:

1. Process for the preparation of fluoroalkyl perfluorovinyl ethers of the formula $$Y-R_f-O-(CF-CF_2-O)_n-CF=CF_2 \quad (I)$$
$$\phantom{Y-R_f-O-(}CF_2X$$

wherein:
Y is Br or F;
X is F, Cl or Br or their mixtures when n is equal to or higher than 2;
n is within the range of from 0 to 4;
$R_f$ represents a perfluoroalkylene radical containing from 1 to 8 C atoms;
characterized in that a fluoroalkoxy perfluoroacyl fluoride of the formula:

$$Y-R_f-O-(CF-CF_2-O)_n-CF-COF \quad (II)$$
$$\phantom{Y-R_f-O-(}CF_2X \phantom{-CF_2-O)_n-}CF_3$$

is slowly heated with a salifying agent and a solvent, in the presence of a catalytic amount of N,N-dimethylformamide, with an end temperature within the range of from 60° to 150° C.

2. Process according to claim 1, characterized in that the amount of N,N-dimethylformamide is within the range of from 0.1 to 20% by weight relative to the fluoroalkoxy perfluoroacyl fluoride (II).

3. Process according to claim 1, characterized in that the amount of N,N-dimethylformamide is within the range of from 0.5 to 5% by weight relative to the fluoroalkoxy perfluoroacyl fluoride (II).

4. Process according to claims 1, 2 or 3 characterized in that the solvent is selected from the group consisting of the glymes.

5. Process according to claim 1, 2 or 3 characterized in that the salifying agent is selected from the group consisting of the carbonates of alkali and alkali-earth metals.

6. Process according to claim 5 characterized in that the salifying agent is an alkali metal carbonate.

7. Process according to claims 1, 2 or 3 characterized in that in the fluoroalkoxy perfluoroacyl fluoride (II), the value of n is zero.

8. Process according to claims 1, 2 or 3 characterized in that in the fluoroalkoxy perfluoroacyl fluoride (II), the radical $R_f$ contains from 2 to 3 C atoms.

9. Process according to claims 1, 2 or 3, characterized in that an end temperature within the range of from 110° to 140° C. is reached.

* * * * *